US005625043A

United States Patent [19]
Priebe et al.

[11] Patent Number: 5,625,043
[45] Date of Patent: Apr. 29, 1997

[54] ANTHRACYCLINES WITH UNUSUALLY HIGH ACTIVITY AGAINST CELLS RESISTANT TO DOXORUBICIN AND ITS ANALOGS

[75] Inventors: Waldemar Priebe, 4239 Emory, Houston, Tex. 77005; Piotr Skibicki, 04-015 Warsaw, ul. Waszyngtona 39m.24, Poland; Roman Perez-Soler, 2906 Ria Blvd., Houston, Tex. 77005

[73] Assignees: Waldemar Priebe; Piotr Skibicki; Roman Perez-Soler, Houston, Tex.

[21] Appl. No.: 396,290

[22] Filed: Feb. 27, 1995

Related U.S. Application Data

[63] Continuation of Ser. No. 31,173, Mar. 12, 1993, abandoned.
[51] Int. Cl.$^6$ ................................................ C07M 15/24
[52] U.S. Cl. ................................................................ 536/6.4
[58] Field of Search ................................. 536/6.4; 514/34

[56] References Cited

U.S. PATENT DOCUMENTS

| | | | |
|---|---|---|---|
| 4,201,773 | 5/1980 | Horton et al. | 536/6.4 |
| 4,327,029 | 4/1982 | Bernardi et al. | 260/351.1 |
| 4,427,664 | 1/1984 | Horton et al. | 424/180 |
| 4,537,882 | 8/1985 | Horton et al. | 514/34 |
| 4,562,177 | 12/1985 | Horton et al. | 514/34 |
| 4,663,445 | 5/1987 | Swenton et al. | 536/6.4 |
| 4,697,005 | 9/1987 | Swenton et al. | 536/6.4 |
| 4,863,739 | 9/1989 | Perez-Soler et al. | 424/450 |
| 4,870,058 | 9/1989 | Horton et al. | 514/34 |
| 5,132,290 | 7/1992 | Priebe et al. | 514/34 |

FOREIGN PATENT DOCUMENTS

PCT/US94/02619  6/1994  WIPO.

OTHER PUBLICATIONS

Bodley et al., "N-Alkyl Analogs of Doxorubicin Do Not Inhibit DNA Topoisomerase II," *Proc. Ann. Meet. Am. Assoc. Cancer Res.*, 30:621, Abstract No. 2472, 1989.

Ganapathi et al., "N-Benzyladriamycin-14-valerate Versus Progressively Doxorubicin-Resistant Murine Tumours: Cellular Pharmacology and Characterisation of Cross-Resistance in vitro and in vivo," *Br. J. Cancer*, 60:819–826, 1989.

Goodman and Gilman's, "The Pharmacological Basis of Therapeutics," Eighth Edition, Pergamon Press, Chapter 52, pp. 1241–1244.

Israel et al., "Amelioration of Adriamycin Toxicity Through Modification of Drug-DNA Binding Properties," *Cancer Treatment Reviews*, 14:163–167, 1987.

Lothstein et al., "Resistance to N-Benzyladriamycin-14-valerate in Mouse J744.2 Cells: P-Glycoprotein Expression without Reduced N-Benzyladriamycin-14-valerate Accumulation," *Cancer Research*, 52:3409–3417, 1992.

O'Dwyer et al., "Drug Therapy. Etoposide (VP-16-213). Current Status of an Active Anticancer Drug," *The New England Journal of Medicine*, 312:692–700, 1985.

Priebe et al., "Novel Anthracycline Antibiotics Deoxygenated at C-4'", *Proc. Ann. Meet. Am. Assoc. Cancer Res.*, 30:575, Abstract No. 2287, 1989.

Remington's Pharmaceutical Sciences, Alfonso R. Gennaro, Editor, Eighteenth Edition, Chapter 61, pp. 1150–1151, 1990.

Cheung et al., "Preparative Synthesis of 2,6-dideoxy-α-L-lyxo-Hexose (2-Deoxy-α-L-Fucose) and its D-ribo Epimer (Digitoxose)" *Carbohydrate Research* 58:139–151, (1977).

*Primary Examiner*—Elli Peselev
*Attorney, Agent, or Firm*—Arnold, White & Durkee

[57] ABSTRACT

The present disclosure details novel modified anthracyclines, the synthesis thereof, and their use in treating patients with tumors. Preferred aspects of the disclosure involve modified anthracyclines which have an O-substituted aromatic ring on their sugar moiety. Other preferred aspects of the disclosure involve synthesis steps wherein a hydroxyl group on a sugar moiety to be added is blocked with a halo-substituted alkyl group during the process of adding it to an anthracycline ring compound.

19 Claims, 3 Drawing Sheets

ANTHRACYCLINES WITH UNUSUALLY HIGH ACTIVITY AGAINST CELLS RESISTANT TO DOXORUBICIN AND ITS ANALOGS

This application is a continuation of application Ser. No. 08/031,173, filed Mar. 12, 1993, now abandoned.

BACKGROUND OF THE INVENTION

1. Field of the Invention

This application relates generally to the treatment of cancer. Specifically, the invention relates to novel compounds useful for chemotherapy, methods of synthesis of these compounds, and methods of treatment employing these compounds. The novel compounds described are analogs of the doxorubicin which is known to have anti-tumor effects.

2. Description of the Related Art

Resistance of tumor cells to the killing effects of chemotherapy is one of the central problems in the management of cancer. It is now apparent that at diagnosis many human tumors already contain cancer cells that are resistant to standard chemotherapeutic agents. Spontaneous mutation toward drug resistance is estimated to occur in one of every $10^6$ to $10^7$ cancer cells; this mutation rate appears to be independent of any selective pressure from drug therapy, although radiation therapy and chemotherapy may give rise to additional mutations and contribute to tumor progression within cancer cell populations (Goldie et al., *Cancer Treat. Rep.*, 63:1727, 1979; Goldie et al., *Cancer Res.*, 44:3643, 1984; and Nowell, *Cancer Res.*, 46:2203, 1986). The cancer cell burden at diagnosis is therefore of paramount importance because even tumors as small as 1 cm ($10^9$ cells) could contain as many as 100 to 1,000 drug-resistant cells prior to the start of therapy.

Selective killing of only the tumor cells sensitive to the drugs leads to an overgrowth of tumor cells that are resistant to the chemotherapy. Mechanisms of drug resistance include decreased drug accumulation (particularly in multidrug resistance), accelerated catabolism of the drug and other alterations of drug metabolism, and an increase in the ability of the cell to repair drug-induced damage (Curt et al., *Cancer Treat. Rep.*, 68:87, 1984; and Kolate, *Science*, 231:220, 1986). The cells that overgrow the tumor population not only are resistant to the agents used but also tend to be resistant to other drugs, many of which have dissimilar mechanisms of action. This phenomenon, called pleiotropic drug resistance or multidrug resistance (MDR), may account for much of the drug resistance that occurs in previously treated cancer patients.

Gene amplification (i.e., the production of extra copies of genes within a cell) is one of the mechanisms that can lead to drug resistance. Gene amplification is involved in the phenomenon of multidrug resistance. Multidrug resistance appears to be linked to over-expression of a cell membrane glycoprotein, termed P-glycoprotein, on the surface of cancer cells (Bell et al., *J. Clin. Oncol.*, 3:311, 1985; and Bertino, *J. Clin. Oncol.*, 3:293, 1985). The action of this glycoprotein is unknown, but its over-expression is associated with decreased accumulation of multiple chemotherapeutic drugs within the resistant cells. A multidrug-resistance gene that encodes the P-glycoprotein has been isolated and sequenced, and when it is transferred, this gene confers drug resistance on previously drug-sensitive cells (Gros et al., *Nature*, 323:728, 1986). The multidrug-resistance gene termed mdrl is expressed in several normal tissues, and its expression is increased in some human tumors (Fojo et al., *P.N.A.S.*, 84:265, 1987). Various human tumors are now being analyzed to determine whether they express this gene. Because many heavily treated patients who are in relapse harbor tumors that do not show over-expression of the mdrl gene, it appears that other mechanisms are probably also involved in causing resistance to chemotherapy.

The commonly used chemotherapeutic agents are classified by their mode of action, origin, or structure, although some drugs do not fit clearly into any single group. The categories include alkylating agents, antimetabolites, antibiotics, alkaloids, and miscellaneous agents (including hormones); agents in the different categories have different sites of action.

Antibiotics are biologic products of bacteria or fungi. They do not share a single mechanism of action. The anthracyclines daunorubicin and doxorubicin (DOX) are some of the more commonly used chemotherapeutic antibiotics. The anthracyclines achieve their cytotoxic effect by several mechanisms, including intercalation between DNA strands, thereby interfering with DNA and RNA synthesis; production of free radicals that react with and damage intracellular proteins and nucleic acids; chelation of divalent cations; and reaction with cell membranes. The wide range of potential sites of action may account for the broad efficacy as well as the toxicity of the anthracyclines (Young et al., *N. Engl. J. Med.*, 312:692, 1985).

The anthracycline antibiotics are produced by the fungus *Streptomyces peucetius var. caesius*. Although they differ only slightly in chemical structure, daunorubicin has been used primarily in the acute leukemias, whereas doxorubicin displays broader activity against human neoplasms, including a variety of solid tumors. The clinical value of both agents is limited by an unusual cardiomyopathy, the occurrence of which is related to the total dose of the drug; it is often irreversible. In a search for agents with high antitumor activity but reduced cardiac toxicity, anthracycline derivatives and related compounds have been prepared. Several of these have shown promise in the early stages of clinical study, including epirubicin and the synthetic compound mitoxantrone, which is an amino anthracenedione.

The anthracycline antibiotics have tetracycline ring structures with an unusual sugar, daunosamine, attached by glycosidic linkage. Cytotoxic agents of this class all have quinone and hydroquinone moieties on adjacent rings that permit them to function as electron-accepting and donating agents. Although there are marked differences in the clinical use of daunorubicin and doxorubicin, their chemical structures differ only by a single hydroxyl group on C14. The chemical structures of daunorubicin and doxorubicin are as follows:

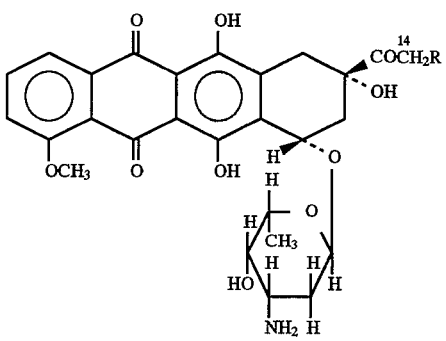

Daunorubicin: R = H
Doxorubicin: R = OH

Unfortunately, concomitant with its antitumor activity, DOX can produce adverse systemic effects, including acute myelosuppression, cumulative cardiotoxicity, and gastrointestinal toxicity (Israel et al., *Cancer Treat. Rec.*, 14:163, 1987). At the cellular level, in both cultured mammalian cells and primary tumor cells, DOX can select for multiple mechanisms of drug resistance that decrease its chemotherapeutic efficacy. These mechanisms include P-gp-mediated MDR, characterized by the energy-dependent transport of drugs from the cell (Bradley et al., *Biochem. Biophys. Acta.*, 948:87, 1988), and resistance conferred by decreased topoisomerase II activity, resulting in the decreased anthracycline-induced DNA strand scission (Danks et al., *Cancer Res.*, 47:1297, 1987; Pommier et al., *Cancer Res.*), 46:3075, 1986; Moscow et al., *J. Natl. Cancer Inst.*, 80:14, 1988.

Among the potential avenues of circumvention of systemic toxicity and cellular drug resistance of the natural anthracyclines is the development of semisynthetic anthracycline analogues which demonstrate greater tumor-specific toxicity and less susceptibility to various forms of resistance. One such analogue, AD 198, exhibits a variety of mechanistic differences compared with anthracycline, including weaker binding to purified DNA, preferential inhibition of RNA versus DNA synthesis, irreversible $G_2/M$ blockade, pronounced membrane lytic activity, and a lack of inhibition of purified mammalian topoisomerase II despite significant levels of protein-associated DNA strand breaks in alkaline elution assays (Israel et al., 1987; Traganos et al., *Cancer Res.*, 45:6273, 1985; Bodley et al., *Cancer Res.*, 49:5969; and Israel et al., *Cancer Chemother. Pharmacol.*, 25:177, 1989). When compared with anthracycline, AD 198 demonstrates enhanced cytotoxicity against cultured murine and human tumor cells and the ability to circumvent MDR in P388 and L1210 leukemic cells and B16-BL6 melanoma cells, and both MDR and resistance due to altered topoisomerase II activity in variant CCRF-CEM leukemic cells (Ganapath, et al., *Br. J. Cancer*, 60:819, 1989; Sweatman et al., *J. Cell. Pharmacol.*, 1:95–102). Unfortunately, despite the high degree of toxicity seen in vitro, AD 198 exhibits limited efficacy against transplanted MDR L1210 cells in vivo. This observation suggests that resistance to AD 198 may be conferred either systemically through enhanced drug metabolism or pharmacologic sanctuary of the neoplasia or through cellular resistance (Ganapathi et al.).

AD 198 is an anthracycline analogue designed to circumvent MDR and thereby enhance chemotherapeutic efficacy against drug-resistant neoplastic cells. Circumvention of MDR by AD 198 appears to be due, at least in part, to the inability of P-gp to transport AD 198 from the cell (Sweatman et al.). Cellular resistance to AD 198 can emerge rapidly within murine macrophage-like J774.2 cells and with characteristics that were similar to those of MDR. However, AD 198$^R$ cells differ from MDR cells in the persistence of high levels of intracellular AD 198 similar to that of drug-sensitive cells. Resistance to AD 198 could limit the successful utilization of this and other highly hydrophobic anthracycline analogues in the treatment of MDR tumor cells. In addition, it has been shown that MDR J774.2 selected with vinblastine were cross-resistant to AD 198. This finding was in contrast to previous studies showing the ability of AD 198 to circumvent MDR in lymphocytic and melanoma cell lines selected with either anthracycline or vinblastine (Ganapathi et al.; Sweatman et al.), suggesting that cell type may have a significant effect upon the MDR phenotype which emerges in response to challenge with a particular drug.

A further example of cell type effecting the drug resistance phenotype with regard to a particular drug is seen in the various particular AD 198 resistant cells. Two types of AD 198-resistant cells are the AD 198$^R$ cells, which are created by selecting AD 198 resistant cells from the normally AD 198 susceptible J774.2 cells, and the A300 cells, which are created by selecting cells with even greater resistance to AD 198 than the normally resistant A100 cells (Lothstein et al. *Cancer R.*, 52:3409 (1992). Although both AD 198$^R$ cells and A300 cells are resistant to AD 198, the basis of the resistance appears to be different between the cell types (Lothstein).

The development of drug resistance is one of the major obstacles in the management of cancer. There are various types of drug resistance, for example, classic MDR as opposed to AD 198 resistance. Furthermore, different cell lines can establish resistance to the same drug in different ways, as seen in the case of the differences in AD 198 resistance in AD 198$^R$ cells as opposed to A300 cells. One of the traditional ways to attempt to circumvent this problem of drug resistance has been combination chemotherapy.

Combination drug therapy is the basis for most chemotherapy employed to treat breast, lung, and ovarian cancers as well as Hodgkin's disease, non-Hodgkin's lymphomas, acute leukemias, and carcinoma of the testes.

Combination chemotherapy uses the differing mechanisms of action and cytotoxic potentials of multiple drugs. Although all chemotherapeutic drugs are most effective on cells that are active in DNA synthesis, many agents—particularly the alkylating agents—can kill cells that are not cycling. Such agents are termed non-cell proliferation-dependent agents can shrink tumor mass by reducing cell numbers; the surviving cells will then move into the cycling compartment, where they are more susceptible to cell proliferation-dependent drugs. The combined use of agents less dependent on the cell cycle followed by those dependent on cell proliferation is effective in enhancing tumor cell death. Each cycle of treatment kills a fixed fraction of cells, so repetitive cycles are required for cure. For example, a drug combination that kills 99.9 percent of cancer cells per treatment cycle would have to be repeated at least six times to eliminate an average tumor burden (if tumor cells did not regrow between cycles).

Although combination chemotherapy has been successful in many cases, the need still exists for new anti-cancer drugs. These new drugs could be such that they are useful in conjunction with standard combination chemotherapy requires. Or, these new drugs could attack drug resistant tumors by having the ability to kill cells of multiple resistance phenotypes. For example, a drug that has the ability to kill cells with both MDR and AD 198 resistance could eliminate two populations of resistant cells from a tumor.

A drug that exhibits the ability to overcome multiple drug resistances could be employed as a chemotherapeutic agent either alone or in combination with other drugs. The potential advantages of using such a drug in combination with chemotherapy would be the need to employ fewer toxic compounds in the combination, cost savings, and a synergistic effect leading to a treatment regime involving fewer treatments.

SUMMARY OF THE INVENTION

This invention involves novel compounds that have utility as anti-tumor and/or chemotherapeutic drugs, methods of synthesizing these compounds, and methods of using these compounds to treat patients with cancer. It has been discovered that anthracycline derivatives that have aromatic rings attached to their sugar moiety have a surprisingly strong ability to kill tumor cells. Furthermore, these compounds are effective against cells with any of a variety of different forms of drug resistance, for example: MDR, AD 198 resistance, and vinblastine resistance. In light of this surprisingly broad cytotoxic ability, the compounds of the present invention exhibit potential for use as chemotherapeutic drugs. The aromatic substitution in the more specific embodiments of these compounds is made using an oxygen linkage from C-3 of the sugar moiety. Doxorubicin and doxorubicin analogs have an amine group attached to C-3, and this is replaced in the compounds of this invention.

The anthracycline derivatives that have these modifications have been shown to have the ability to kill tumor cells which are resistant to known chemotherapeutic agents, including doxorubicin and modified anthracycline derivatives. For example, two of these compounds which are O-benzylated at the 3' carbon of the sugar moiety, WP 546 and WP 549, have very high cytotoxicity against tumor cells that are resistant to doxorubicin, AD 198, and vinblastine. Specifically, these compounds have been shown to kill KB V1 cells and J774.2 cells, both of which exhibit classic MDR to doxorubicin. Further, these compounds have demonstrated cytotoxicity against AD 198 resistant cells such as J7/A300 cells and P388 cells. Finally, these compounds have been shown to have cytotoxic effects against J7/40V cells, which are resistant to vinblastine. This is a surprising result in that resistance to these three compounds occurs by differing mechanisms. Therefore, WP 546 and WP 549 have the ability to overcome all of these mechanisms of drug resistance.

Because of they exhibit the ability to kill many types of resistant tumor cells, WP 546, WP 549,and other anthracycline derivatives that have aromatic rings substituted on their sugar moieties should be of great utility as chemotherapeutic compounds. Chemotherapeutic regimes usually involve a combination of agents. This combination therapy is necessitated by the presence of populations of cells within a tumor that may be resistant to one or another of the individual drugs used. Furthermore, even a combination therapy may not be available for some forms of tumors. Given that the compounds claimed in this application exhibit a broad cytotoxic ability against a variety of cells with a variety of differing drug resistances, the need for combination therapy may be reduced by the present compounds. For example, it may be that only one chemotherapeutic agent comprising one of these compounds is required to treat a tumor. Likewise, it may be that the need for combinations of agents still exists, but that the number of toxic compounds introduced into a patient may be reduced. For example, instead of a combination therapy in which doxorubicin, AD 198, vinblastine, and other agents are required to kill all of a particular type of tumor, WP 549 can replace the doxorubicin, AD 198, and vinblastine. Obviously, there are huge potential benefits to reducing the number of chemotherapeutic agents given to a patient, as each agent is a toxin and potentially has its own specific side-effects and cross reactions with other compounds.

The Inventors have also found that the substitution of an alkyl-halosubstituted group, particularly a fluoro-methyl group, for the C-6 methyl group of the sugar moiety of these anthracycline analogs can have the surprising effect of stabilizing the molecule. This stabilization could result in compounds that exhibit this fluoro-methyl substitution being more active than those which do not. The Inventors' hypothesis is that this alkyl-halo substitution will be of benefit in many anthracycline derivatives, not only those that have aromatic ring substitutions on their sugar moieties.

The general structural formula of these novel compounds of the present invention is:

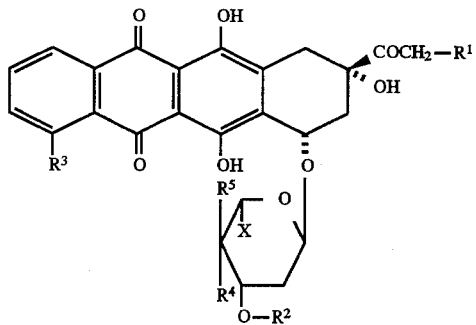

In these compounds, $R^1$ can be almost any form of organic group such as a hydrogen, a hydroxyl group, an alkyl group, an arylalkyl group, an alkyl in ester linkage group, or the like. Preferred embodiments of the invention will have a hydroxyl group at $R^1$. In some preferred embodiments of the invention, the $R^1$ hydroxyl group will be acylated. In the most preferred embodiments of these novel compounds, the $R^1$ hydroxyl group will be either a free hydroxyl group or O-valerate. WP 546 and WP 549 are examples of these most preferred embodiments.

$R^2$ is the O-substituted moiety on the sugar portion of the anthracycline compound. $R^2$ is typically a $CH_2$—Ar group, where Ar is further defined as being an aryl group such as benzene, toluene, xylene, mesitylene, cumene, cymene, styrene, naphthalene, etc. In preferred embodiments of the claimed compounds, the Ar group at $R^2$ will be a phenyl ring. In other words, the sugar molecule will be O-benzylated at C-3. In the fluoro-methylated forms of the compounds, $R^2$ need not necessarily be a $CH_2$—Ar group and could potentially be a hydrogen, a hydroxyl group, an alkyl group, an arylalkyl group, or an alkyl in ester linkage group.

Those of skill in the art will appreciate that many potential modifications could be made at various points on the claimed compounds, with minimal effort and using standard organic synthesis techniques. Potential sites for such modification can be almost anywhere on the molecule, for example, at those denoted $R^1$, $R^3$, $R^4$, and $R^5$ in the above structure Potential modifications could be having the various sites substituted with, for example, a hydrogen, a hydroxyl group, an alkyl group, an arylalkyl group, or an alkyl in ester linkage group. However, in most of the compounds, $R^3$ is a hydrogen or $OCH_3$ group, while $R^4$ and $R^5$ are either hydrogen or hydroxyl groups.

The Inventors have found that a 6-fluoro group at X on the sugar moiety can have a stabilizing effect on anthracycline structures. A 6-fluoro-methyl group has been used for this purpose, and it is anticipated that many alkyl-halosubstituted groups will have such utility. Therefore, X is either an alkyl or alkyl-halosubstituted group. In preferred embodiments on the invention, the X portion of the compound will be either a methyl group or a fluoro-methyl group. In a preferred embodiment, X is a methyl group. In another preferred embodiment, X is a fluoro-methyl group while $R^2$ is a hydrogen. In other preferred embodiments of the present invention, X is a methyl group and Ar is a phenyl group.

The most preferred embodiments of the present invention are WP 546 and WP 549. WP 546 (7-O-(3-O-benzyl-2,6-dideoxy-α-L-lyxo-hexopyranosyl)adriamycinone), has a free hydroxyl group at $R^1$, a benzyl group at $R^2$, an $OCH_3$ group at $R^3$, a free hydroxyl group at $R^4$, a hydrogen at $R^5$, and a methyl group at X. WP 549 (7-O-(3-O-benzyl-2,6-dideoxy-α-L-lyxo-hexopyranosyl)-14-O-valeroyl-adriamycinone) is the same as WP 546, except that it has an O-valerate group at $R^1$. The structures of WP 546 and WP 549 are as follows:

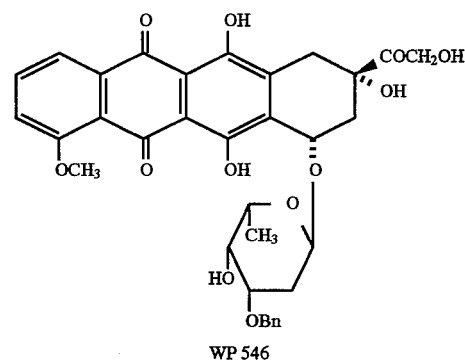

WP 546

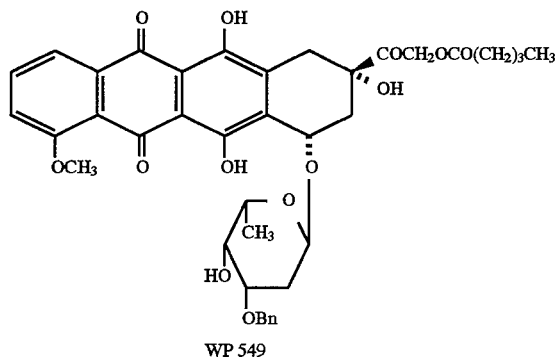

WP 549

Of course, those of skill in the art understand that minor modifications in the above described embodiments of the present invention are possible. Such modified compounds are also covered by this application. For example, it would be possible to modify the basic structure of the compounds at other sites, such as Z and Y on the structure below:

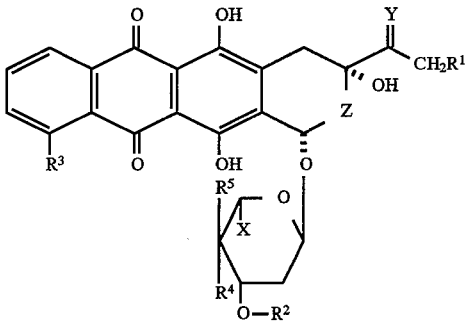

In this modified structure, the Z site could be CHF, $CF_2$, O, N or S, while the Y site could be O; H,H; or H,OH. Any of these modifications could be readily made by those of skill in the art.

Other aspects of the present invention involve the synthesis of the novel compounds described above. During the elucidation of the synthesis processes, the inventors found that, surprisingly, the standard organic chemistry step of blocking the hydroxy group at C-4 on the sugar with an acetyl group did not work because the blocking group could not later be removed. The inventors hypothesis that this effect was due to the presence of the benzyl group on the sugar. Therefore, the inventors attempted blocking of the hydroxyl group at C-4 with trifluoroacetate. Trifluoroacetate is typically considered to be too weak of a blocker to have utility in such a synthesis. However, the use of trifluoroacetate was found to have surprisingly utility in the present synthesis. In preferred embodiments of the synthesis methods the C-4 hydroxyl group on the sugar will be blocked with trifluoroacetate.

Two specific examples of the disclosed compounds have been synthesized. These are WP 546, and WP 549. The preferred method of synthesis of the sugar moiety of both of these compounds is shown in FIG. 1. Further, the preferred synthesis of WP 549 is in FIG. 2, while that of WP 546 is in FIG. 3. In depth descriptions of the synthetic reactions and conditions of these compounds is found in Example I of the Detailed Description of the Preferred Embodiments section of the application.

The 6-halo-alkyl sugars that are required for some embodiments of the present invention can be easily synthesized. For example, 6-fluoro sugars can be prepared by direct fluorination of L-sugars containing 6-hydroxy substituents. Two major approaches may be used to do this: 1) the hydroxyl group can be derived to form an easy leaving group (OM, OT, OTf, etc.) and subsequent nucleophilic substitution of fluoride can occur; or 2) the fee hydroxyl compound can be directly reacted with diethylaminosulfur triflouride (DAST). As an example of the preferred second approach, methyl-α-L-glucopyranoside was transformed into methyl 6-deoxy-6-fluoro-α-L-glucopyranoside. The experimental details are given in the Preferred Embodiments section. Such 6-fluoro-hexopyranoses can be further transformed into 3'-OH and 3'-O-benzyl sugars using standard synthetic procedures.

Of course, those skilled in the art will appreciate many potential variations in the synthesis of the above described compounds. These embodiments of the invention are also to be considered part of the present application. For example, 3-O-Benzyl-2,6-dideoxy-hexopyranoses or hexopyranosides could be used as the sugar moiety, for direct coupling with a proper aglycon. Should these different sugar moieties be used, those of skill in the art will understand that different coupling reagents will be necessary, and these are standard in the art. The preferred coupling reagent for use with hexopyranoses and hexopyranosides is trimethylsilyltriflate.

Other aspects of the claimed invention include methods of treating a patient with cancer. These methods involve administering to a patient a therapeutically effective amount of any of the above described novel compounds. It is anticipated that these compounds will have great utility as chemotherapeutic agents. This is especially true in light of the fact that the above described agents exhibit such broad cytotoxic effects.

Figure 1:
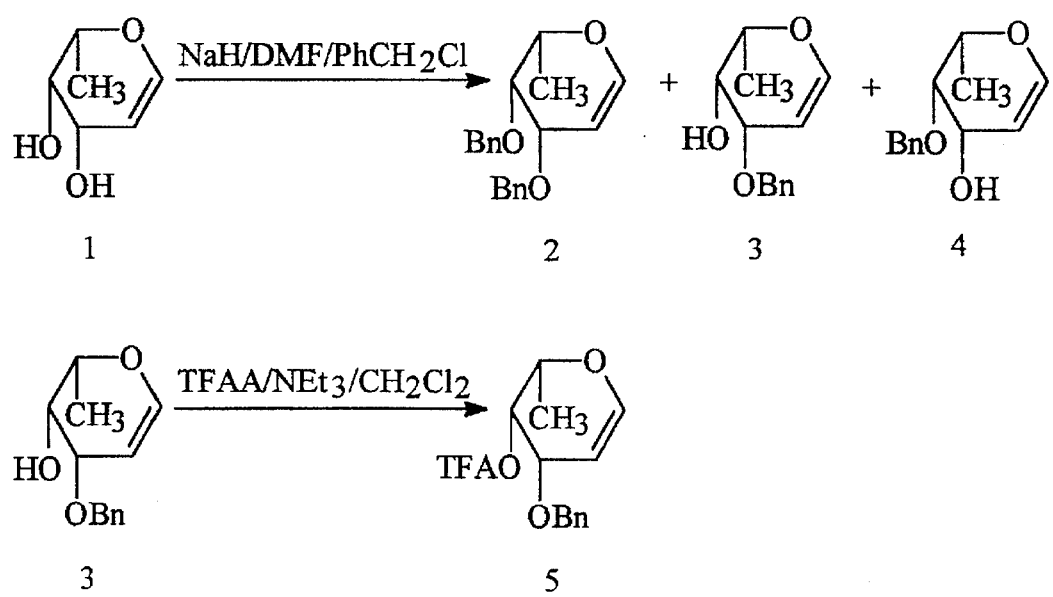
FIG. 1: The synthesis of the sugar portions of WP 549 and WP 546.
Figure 2:
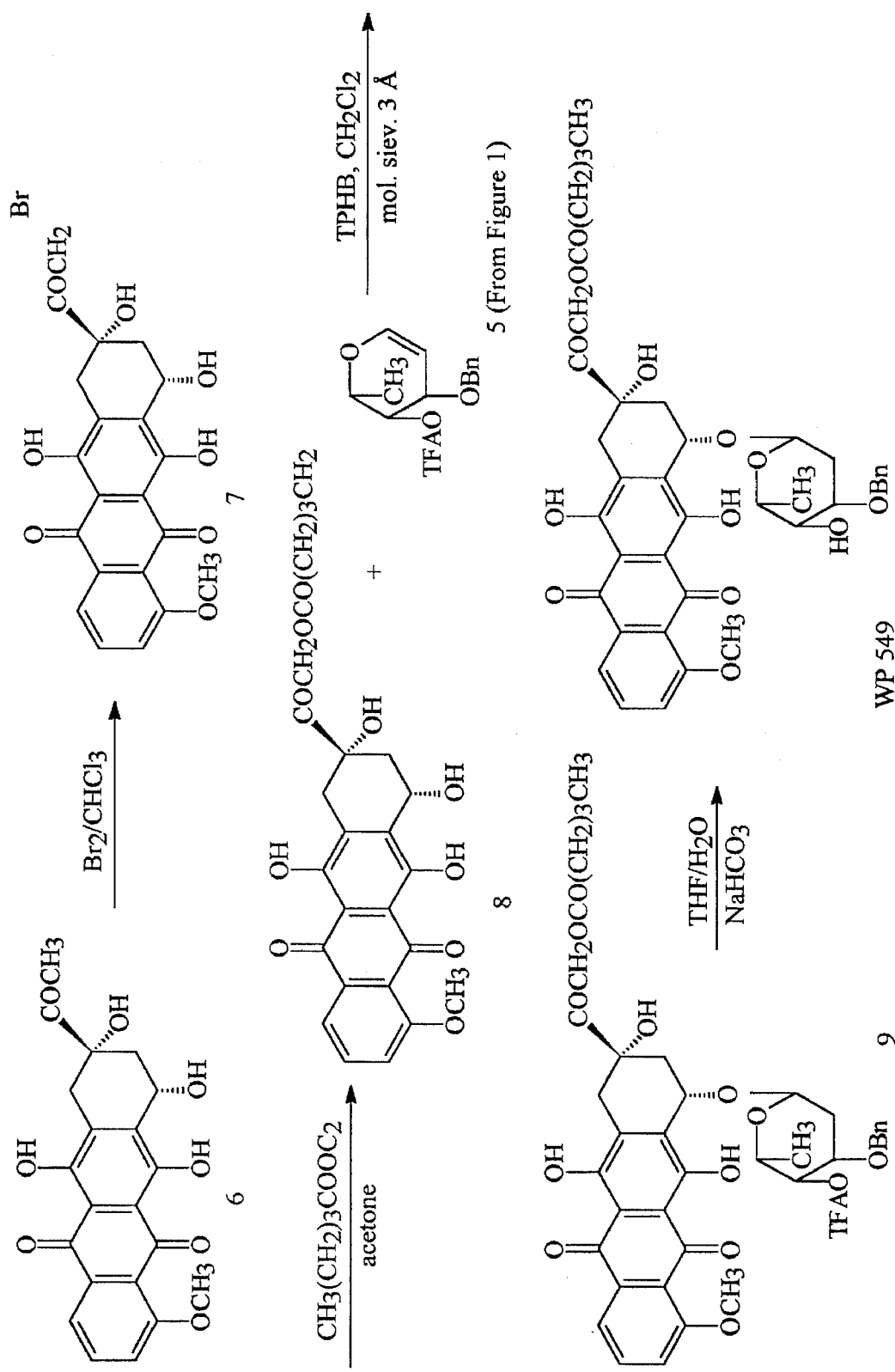
FIG. 2: The synthesis of WP 549.
Figure 3:
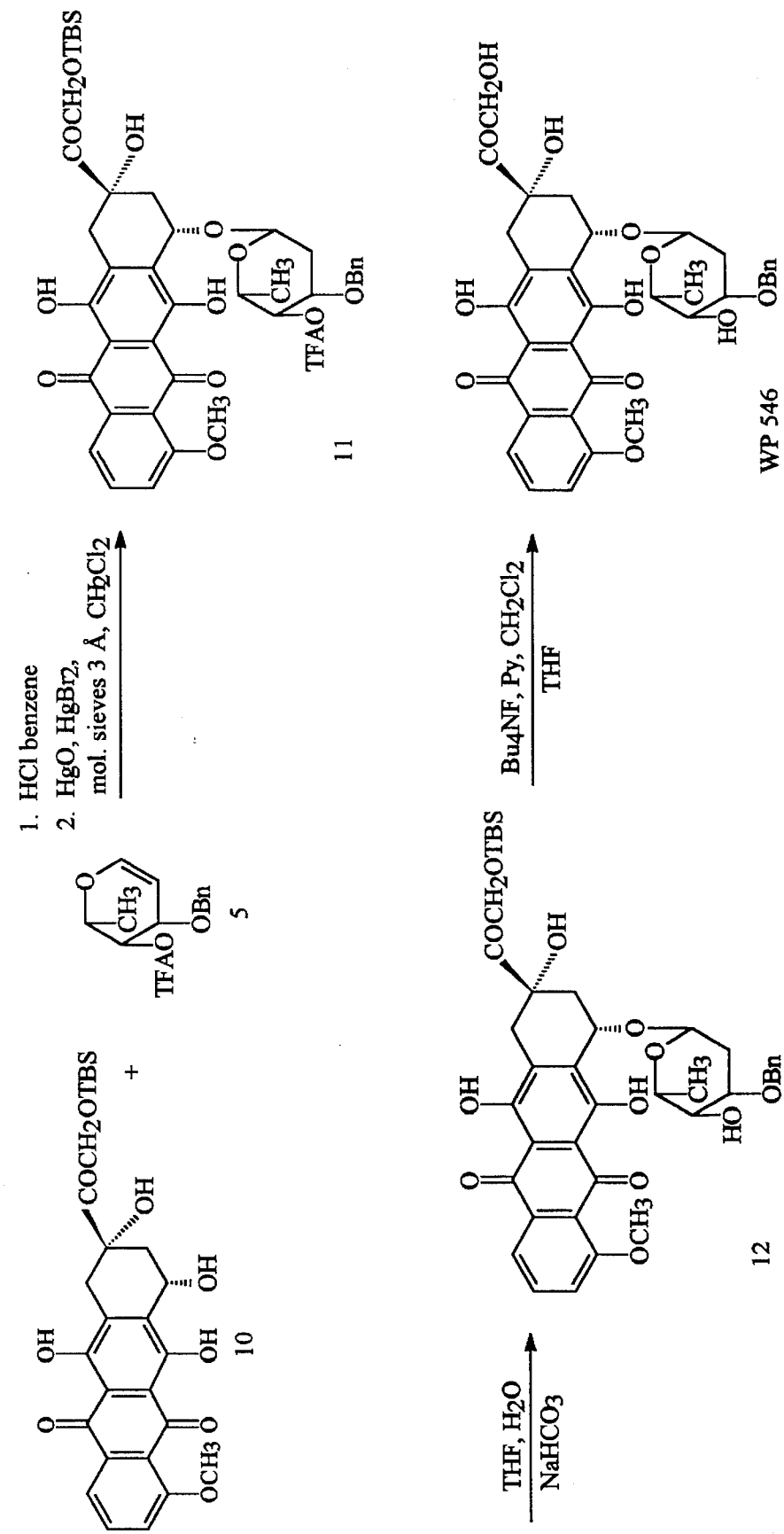
FIG. 3: The synthesis of WP 546.

Key to FIGS. 1–3:
1=L-fucal
2=3,4-di-O-benzyl-L-fucal
3=3-O-benzyl-L-fucal
4=4-O-benzyl-L-fucal
5=3-O-benzyl-4-O-trifluoroacetyl-L-fucal
6=daunomycinone
7=14-bromodaunomycinone
8=14-O-valeroyldaunomycinone
9=7-O-(3-O-benzyl-2,6-dideoxy-4-O-trifluoroacetyl-α-L-lyxo-hexopyranosyl)-14-O-valeroyladriamycinone
10=14-O(t-butyl-dimethylsilyl)-adriamycinone
11=7-O-(3-O-benzyl-2,6-dideoxy-4-O-trifluoroacetyl-α-L-lyxo-hexopyranosyl)-14-O-(t-butyl-dimethylsilyl) adriamycinone
12=7-O-(3-O-benzyl-2,6-dideoxy-α-L-lyxo-hexopyranosyl)-14-O-(t-butyl-dimethylsilyl) adriamycinone
WP 546=7-O-(3-O-benzyl-2,6-dideoxy-α-L-lyxo-hexopyranosyl)adriamycinone
WP 549=7-O-(3-O-benzyl-2,6-dideoxy-α-L-lyxo-hexopyranosyl)-14-O-valeroyladriamycinone

DETAILED DESCRIPTION OF THE PREFERRED EMBODIMENTS

The following examples are included only to demonstrate preferred embodiments of the invention. It should be appreciated by those of skill in the art that the techniques disclosed in the examples represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

In a series of studies demonstrating the surprising and unexpected antitumor activities of the novel compounds of the claimed invention, anthracyclines with the 3'-amino group replaced with O-benzyl substituent and either having the 14-hydroxy group free or acylated were prepared using a multi-step synthesis. All congeners were tested for cytotoxic activity in vitro against doxorubicin (DOX) sensitive and multidrug resistant (MDR) cell lines. The cytotoxic properties of 3'-O-benzyl-doxorubicin were surprisingly similar in DOX-sensitive and DOX-resistant cell lines. The observed activity against the resistant cells was unexpectedly high. The resistant indices were often below the value of 1, indicating higher activity of the inventive compounds against cells resistant to AD 198 or vinblastine than those cells that were not resistant to those drugs (see Tables 1 and 2). The synthesized compounds were shown to have cytotoxic activity against J774.2 cells (DOX resistant), J7/A300 cells, (resistant to DOX and AD 198). Therefore, the novel anthracycline derivatives of the present invention have the ability to kill an unusually broad variety of tumor cells and overcome a variety of drug resistances. As a result, it is anticipated that the novel anthracycline derivatives of the present invention will have great utility in the treatment of tumors.

EXAMPLE I

Preparation of Anthracycline Derivatives:

The 3'-O-benzyl-doxorubicin (WP 546) and its 14-O-valerate ester (WP 549) were prepared from 3-O-benzyl-L-fucal in electrophilic addition reaction using triphenylphosphine hydrobromide (TPHB) and 14-O-acylated aglycone. The synthetic processes are diagramed in FIGS. 1–3, and the numbers in parenthesis after chemical names in the text are keyed in the Figures.

Synthesis of Sugar Portion of Compound

The sugar position of both WP 546 and WP 549 was synthesized as follows. This synthesis is detailed in FIG. 1.

3-O-Benzyl-L-fucal (3) for use in the synthesis of WP 546 and WP 549 was prepared by the following method. L-Fucal (1) (5.36 g, 0.041 mol) in DMF (48 ml) was added to the solution of sodium hydride (60% dispersion in mineral oil, 1.81 g, 0.045 mol) in DMF (125 ml) at 0° C. Then benzyl chloride (5.3 ml, 0.046 mol) was added. The reaction mixture was stirred for 2 hours. Then methanol (53 ml) and water (300 ml) were added and products were extracted with diethyl ether. Organic extract was dried over anhydrous sodium sulfate. Crude reaction mixture was chromatographed on the silica gel column (200 g) in hexane/diethyl ether/methanol 80/20/2 solvent system to give: 1.05 g of 3,4-di-O-benzyl-L-fucal 2 (8.3%), 2.89 g of 3-O-benzyl-L-fucal (3) (32%) and 3.40 g of 4-O-benzyl-L-fucal (4) (37.6%).

Next, 3-O-Benzyl-4-O-trifluoroacetyl-L-fucal (5) was synthesized. 3-O-benzyl-L-fucal (3) (1.09 g, 4.94 mmol) was dissolved in dichloromethane (44 ml) under nitrogen and triethylamine (13.3 ml) was added. The reaction mixture was cooled down (ice bath) and trifluoroacetic anhydride (6.8 ml, 48.14 mmol) was added. After 2 hours there was no substrate in the reaction mixture. Solvent was evaporated in vacuo and the reaction mixture was dried under high vacuum. Crude reaction mixture was chromatographed on the silica gen column (60 g) in hexane/ethyl acetate 95/5 solvent system to give 997.2 mg (63.8%) of 3-O-benzyl-4-O-trifluoroacetyl-L-fucal (5) which could then be used in the following synthesis reactions.

Synthesis of WP 549

7-O-(3-O-benzyl-2,6-dideoxy-α-L-lyxo-hexopyranosyl)-14-O-valeroyladriamycinone (WP 549), was synthesized according to the scheme detailed in FIG. 2.

Briefly the synthesis was as follows:

14-Bromodaunomycinone (7) was first prepared. Daunomycinone (6) (360.2 mg, 0.90 mmol) was dissolved in anhydrous chloroform (45 ml). Then solution A (3.1 g of $Br_2$ in 30 ml of $CHCl_3$). (9.6 ml) was added. The reaction mixture was stirred at the room temperature for 4 hours. Then the reaction mixture was diluted with hexane and the precipitate was filtered off. This precipitate was dissolved in chloroform and the resulting solution was concentrated in vacuo. 14-Bromodaunomycinone (7) (353.1 mg, 81.1%) was filtered off and washed with hexane.

14-O-Valeroyldaunomycinone (8) was then synthesized as follows. 14-Bromodaunomycinone (7) (206.6 mg, 0.43 mmol) was dissolved in dry acetone (80 ml) and cesium valerate (200 mg, 0.85 mmol) was added. After 15 min. reaction mixture was diluted with dichloromethane, washed with water and dried over anhydrous sodium sulfate. 14-O-Valeroyldaunomycinone (8) (180.4 mg, 83.6%) was precipitated from dichloromethane/hexane solvent system and separated by centrifugation.

14-O-substituted anthracyclines such as the 14-O-valeroyldaunomycinone prepared above have been previously prepared by nucleophilic substitution of 14-bromo derivatives using sodium or potassium salts of carboxylic acids. The Inventors have found that the synthesis can be performed with higher yield and higher purity when cesium salts were used. As an example, cesium valerate was synthesized and successfully used towards preparation of the 14-O-valeroyl derivative (9). To prepare cesium valerate, a solution of cesium carbonate (20 g) in anhydrous methyl alcohol (480 ml) was added to a solution of valeric acid (20 ml) in methyl alcohol (120 ml). After addition, the reaction mixture was stirred for 30 min. Then methyl alcohol was removed in vacuo and crystalline residue was washed with diethyl ether (10 times) and dried under high vacuum to give 13.6 g (95.3%) of cesium valerate.

7-O-(3-O-Benzyl-2,6-dideoxy-4-O-trifluoroacetyl-$\alpha$-L-lyxo-hexopyranosyl)-14-O-valeroyladriamycinone (9) was prepared as follows. 14-O-Valeroyldaunomycinone (8) (120.2 mg, 0.24 mmol) was dissolved in dry dichloromethane (23 ml) and then TPHB (triphenylphosphine hydrobromide) (306.7 mg, 0.89 mmol, 0.76 eq), molecular sieves (3 Å,600 mesh, 210 mg) and 3-O-benzyl-4-O-trifluoroacetyl-L-fucal 5 (369.0 mg, 1.17 mmol, 4.9 eq.) were added. After 24 hours reaction was completed. The reaction mixture was diluted with dichloromethane and washed with 20% aq. solution of sodium bicarbonate, water and dried over anhydrous sodium sulfate. Crude reaction mixture was chromatographed on the silicagel (26 g, flash) column in the toluene/acetone 98/2 solvent system to give 132.1 mg of product 9. Then the polarity of the eluent was increased (toluene/acetone 9/1) and compound 549 (product of hydrolysis of trifluoroacetyl group on the silicagel, 45.8 mg) was collected. Compound 9 (111.4 mg) was precipitated from diethyl ether and WP 549 (22.2 mg) from tetrahydrofuran/diethyl ether/hexane solvent system. Total yield (products 9 and WP 549) was 69.8%

The synthesis of 7-O-(3-O-benzyl-2,6-dideoxy-$\alpha$-L-lyxo-hexopyranosyl)-14-O-valeroyladriamycinone (WP 549) was then completed as follows. Compound 9 (98.5 mg, 0.12 mmol) was dissolved in tetrahydrofuran (12.8 ml) and water (6.5 ml). Then saturated aqueous solution of sodium bicarbonate (0.24 ml) were added and after four hours the reaction mixture was diluted with dichloromethane, washed with water and dried over sodium sulfate. Crude reaction mixture was chromatographed on the silica gel column (6 g) in toluene/acetone solvent system to give 76 mg of fraction containing product 549. WP 549 was further purified by precipitation from tetrahydrofuran/diethyl ether/hexane. Yield after precipitation (69.7 mg) was 80.1%.

Synthesis of WP 546

7-O-(3-O-benzyl-2,6-dideoxy-$\alpha$-L-lyxo-hexopyranosyl) adriamycinone (WP 546) was synthesized according to the scheme detailed in FIG. 2.

Briefly, the synthesis was as follows:

7-O-(3-O-Benzyl-2,6-dideoxy-4-O-trifluoroacetyl-$\alpha$-L-lyxo-hexopyranosyl)-14-O-(t-butyl-dimethylsilyl) adriamycinone (11) was first prepared. 3-O-Benzyl-4-O-trifluoroacetyl-L-fucal (5) (200 mg, 0.63 mmol) was dissolved in benzene (12 ml) and dry HCl was bubbled for 15 min. The benzene was evaporated and the reaction mixture A was evaporated with benzene. A mixture of 14-O-(t-butyl-dimethylsilyl)-adriamycinone (10) (131.7 mg, 0.25 mmol), mercury (II) oxide (565 mg, 2.6 mmol), mercury (II) bromide (130.6 mg, 0.36 mmol) and molecular sieves (3 Å, 600 mesh, 580 mg) in dichloromethane (11 ml) was stirred for 40 min. before the reaction mixture A (in 8 ml of dichloromethane) was added. After 1 hour, the reaction mixture was diluted with dichloromethane, filtered and washed with 10% aq. solution of potassium iodide, water, and then dried over anhydrous sodium sulfate. After evaporation of solvents, crude product 11 (337, 15 mg) was used in the next step without further purification.

7-O-(3-O-Benzyl-2,6-dideoxy-$\alpha$-L-lyxo-hexopyranosyl)-14-O-(t-butyl-dimethylsilyl)adriamycinone (12) was then synthesized as follows. Crude product 11 (300 mg) was dissolved in the 1:1 mixture of tetrahydrofuran and water (100 ml), and then 5% aq. sol. of sodium bicarbonate (15 ml) was added. After 3 hours, reaction mixture was diluted with dichloromethane. The organic layer was washed with water and dried over anhydrous sodium sulfate. The crude reaction mixture was chromatographed on the silicagel column (14 g) in toluene/acetone 95/5 to 8/2 solvent system to give 115.8 mg (69.8%) of pure compound 12.

Finally, the synthesis of 7-O-(3-O-Benzyl-2,6-dideoxy-$\alpha$-L-lyxo-hexopyranosyl)adriamycinone (WP 546) was completed using the following steps. To the solution of compound 12 (75.5 mg, 0.10 mmol) in tetrahydrofuran (1.5 ml) solution A (tetrahydrofuran (6 ml), dichloromethane (3 ml), pyridine (150 µl), tetrabutylammonium fluoride (1.0M sol. in tetrahydrofuran, 150 µl) (7.6 ml) was added. After 25 min. the reaction mixture was diluted with dichloromethane, washed with water and dried over anhydrous sodium sulfate. Crude reaction mixture was chromatographed on the silicagel column in dichloromethane/diethyl ether/methanol 90/10/2 solvent system to give 24.0 mg (37.8%) of pure WP 546. WP 546 was precipitated from acetone/diethyl ether/hexane and tetrahydrofuran/hexane.

EXAMPLE II

Activity of WP 549 and WP 546

Cytotoxicity of WP 546 and WP 549 Against Dox-Sensitive and DOX-Resistant Cells

An MTT assay was performed to determine the cytotoxicity of DOX, WP 546, and WP 549 to KB 3-1 (DOX-sensitive) and KB V1 (DOX-resistant) cells. The assay was performed as follows:

Doxorubicin was obtained from the Hospital Pharmacy (Adriamycin, Adria Laboratories, Columbus, Ohio). KB 3-1 human carcinoma and KB V1 were obtained from Dr. Michael M. Gottesman at the National Cancer Institute. KB V1 cells have the MDR phenotype and express glycoprotein P-170 in their membrane (Akiyama et al., *Somat. Cell. Mol. Genet.*, 11:117, 1985; Shen et al., *J. Biol. Chem.*, 261:7762, 1986.). KB 3-1 and KB V1 cells were grown in monolayers in Dulbecco's modified Eagle's medium containing 10% fetal bovine serum. For KB V1 cells, vinblastine was added to the culture medium (final concentration 0.5 µg/ml).

In vitro drug cytotoxicites against KB 3-1 and KB V1 cells were assessed by using the MTT reduction assay, as previously reported (Green et al., *J. Immunol. Methods.*, 70:257, 1984). The MTT dye was obtained from Sigma Chemical Company, St. Louis, Mo. Cells were plated in 96-well microassay culture plates ($10^4$ cells/well) and grown for 24 h at 37° C. in a 5% $CO_2$ incubator. Drugs were then added to the wells to achieve a final drug concentration ranging from 0.1 to 50 μg/ml (eight wells were used for each different concentration). The same volume of 0.9% NaCl solution in water with 1% DMSO was added to control wells. Wells containing culture medium alone without cells were used as blanks. The plates were incubated at 37° C. in a 5% $CO_2$ incubator for 1 h (KB cells). When incubation was complete, 15 μl of stock solution of MTT dye in 0.9% NaCl solution in water was added to each well to achieve a final dye concentration of 0.5 mg/ml. The plate was incubated at 37° C. in a 5% $CO_2$ incubator for 4 h. Subsequently, 100 μl of medium was removed from each well from the upper ]K<id,KD layer, and 100 μl of DMSO was added to solubilize the MTT formazan. Complete solubilization was achieved by placing the plate in a mechanical shaker for 30 minutes at room temperature. The optical density of each well was then measured with a microplate spectrophotometer at a wavelength of 600 nm. The percent cell viability was calculated by the following equation:

$$\% \text{ Cell viability} = \frac{\text{Mean optical density of treated wells}}{\text{Mean optical density of control wells}} \times 100$$

The percent cell viability values obtained were plotted against the drug concentrations used, and the $ID_{50}$ was calculated from the curve. Experiments were repeated at least three time.

Table 1 shows the results of this study.

TABLE 1

CYTOTOXICITY OF WP 546 and WP 549 AGAINST KB AND KBV1 CELL LINES

| DRUG | $ID_{50}$ (μg/ml) | | RI |
|---|---|---|---|
| | KB (S) | KBV1 (R) | |
| Doxorubicin (DOX) | 1.1 | 64.0 | 58.2 |
| WP 546 | 4.6 | 4.1 | 0.9 |
| WP 549 | 8.9 | 4.7 | 0.5 |

As the data in Table 1 indicate, analogs WP 546 and WP 549 were unexpectedly more cytotoxic against MDR cells than against parent cells. ($ID_{50}$ 4.1 and 4.7 μg/ml for KB V1 versus 4.6 and 8.9 μg/ml for both in KB 3.1), while the $ID_{50}$ of doxorubicin against the MDR cells was reached at a concentration of 64 μg/ml. In accordance with these results, the calculated resistance indices (RI=$ID_{50}$ KB V1/$ID_{50}$ KB 3-1) for WP 546 and WP 549 were surprisingly low: 0.9 and 0.5 respectively, whereas the RI for DOX was 58.2.

Based on these results, it is to be concluded that WP 546 and WP 549 have the ability to kill DOX-resistant and vinblastine resistant cells.

Cytotoxicity of WP 546 and WP 549 Against AD 198 Resistant Cells

An MTT assay to determine the cytotoxicity of WP 546 and WP 549 to AD 198-resistant {P 388 (R)} and AD 198-sensitive {P388 (S)} cells was performed in a manner similar to that described above.

Table 2 shows the results of this study:

TABLE 2

CYTOTOXICITY OF WP 546 AND WP 549 AGAINST P388 (S) AND P388 (R) CELL LINES

| DRUG | $ID_{50}$ (μM ± S.E.) | | RI |
|---|---|---|---|
| | P388 (S) | P388 (R) | |
| WP 546 | 0.92 ± 0.36 | 0.69 ± 0.23 | 0.8 |
| WP 549 | 1.41 ± 0.23 | 0.73 ± 0.08 | 0.5 |

WP 546 but especially WP 549 showed surprisingly low RIs. The values of 0.8 and 0.5, respectively, indicate that these analogs are more cytotoxic towards cells selected for the resistance than that of a wild type. These findings have implications that will be further studied in the hope of discovering the mechanism whereby WP 549 is able to overcome this resistance.

These data indicate that such analogs can be useful agents in the treatment of tumors expressing resistance to clinically useful anti-cancer agents, as well as to agents useful in preventing preclinical development of cancer.

Broad Cytotoxicity of WP 546 and WP 549 Against Many Types of Drug Resistances

An assay was run which showed that WP 546 and WP 549 had surprisingly broad cytotoxicity against: murine J774.2 cells resistant to DOX, 15-fold AD 198 resistant J7/A300 cells, and J7/40V selected for 120-fold resistance to vinblastine. This data is presented in Table 3.

TABLE 3

CYTOTOXICITY OF WP 546 AND WP 549 AGAINST J774.2, J7/A300, AND J7/40V CELL LINES

| DRUG | $ID_{50}$ (μM) | | | RI | |
|---|---|---|---|---|---|
| | J774.2 | J7/A300 | J7/40V | J7/A300 | J7/40V |
| Doxorubicin (DOX) | 0.024 | 0.586 | 0.755 | 24 | 31 |
| AD 198 | 0.049 | 0.748 | 0.663 | 15 | 14 |
| WP 546 | 1.10 | 2.43 | 2.35 | 2.2 | 2.2 |
| WP 549 | 1.43 | 2.77 | 3.15 | 1.9 | 2.3 |

In light of their surprisingly broad cytotoxicity, WP 546 and WP 549 may be particularly useful for the treatment of human neoplasms that are naturally resistant to anthracyclines and express P-glycoprotein, such as colon carcinoma, or that have become refractory to anthracycline therapy as a result of acquiring the multidrug-resistance phenotype after prolonged therapy with anthracyclines, vinca alkaloids, or other natural anticancer agents. The unexpected cytotoxic activity of WP 546 and WP 549 against cell lines that are resistant to AD 198 is an important finding since resistance to these cells is not associated with a reduced drug accumulation, thus indicating that WP 546 and WP 549 can overcome resistance to anthracyclines mediated by mechanisms not involving the cell membrane. Therefore, it would appear that WP 546 and WP 549 can overcome anthracycline resistance mediated by different types of mechanisms.

EXAMPLE III

In Vivo Studies of WP 546 and WP 549

WP 546 and WP 549 will be tested in vivo for antitumor activity against murine leukemia L1210, P388, and P388 resistant to doxorubicin. In conjunction with these studies, the acute and subacute toxicity will be studied in mice (LD10, LD50, LD90). In a more advanced phase of testing, the antitumor activity of WP 546 and WP 549 against human xenografts will be assessed and cardiotoxicity studies performed will be done in a rat or rabbit model.

EXAMPLE IV

Treatment of Tumors with WP 546 and WP 549

It is anticipated that treatment with WP 546 and/or WP 549 will be along the lines of the treatment regimes of other anthracyclines and their derivatives. For example, standard treatment with doxorubicin is described in *Remingtons Pharmaceutical Sciences* as follows.

Doxorubicin is administered intravenously to adults at 60 to 75 mg/m$^2$ at 21-day intervals or 25 to 30 mg/m$^2$ on each of 2 or 3 successive days repeated at 3- or 4- week intervals or 20 mg/m$^2$ once a week. The lowest dose should be used in elderly patients, when there is prior bone-marrow depression caused by prior chemotherapy or neoplastic marrow invasion, or when the drug is combined with other myelopoietic suppressant drugs. The dose should be reduced by 50% if the serum bilirubin lies between 1.2 and 3 mg/dL and by 75% if above 3 mg/dL. The lifetime total dose should not exceed 550 mg/m$^2$ in patients with normal heart function and 400 mg/m$^2$ on each of 3 consecutive days, repeated every 4 weeks. Prescribing limits are as with adults. It has been reported that a 96-hr continuous infusion is as effective as and much less toxic than the same dose given by bolus injections.

Of course, modifications of the treatment regimes due to the unique nature of WP 546 and WP 549 are possible and well within the ability of one skilled in the art.

What is claimed is:

1. A compound having a formula:

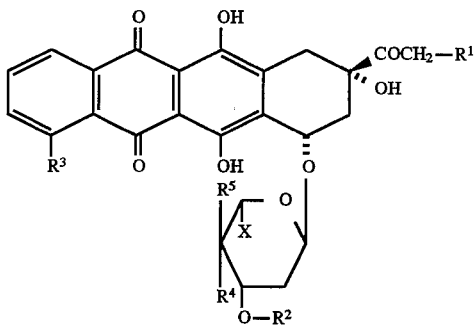

wherein, $R^1$ is a hydrogen, hydroxyl, acylated hydroxyl, alkyl, arylalkyl or alkyl in ester linkage group;

$R^2$ is $CH_2$—AR, where Ar is defined as being an aryl group;

$R^3$ is a hydrogen or $OCH_3$ group;

$R^4$ and $R^5$ are either hydrogen or hydroxyl groups;

X is an alkyl group; and the compound demonstrates the ability to kill a doxorubicin-resistant tumor cell.

2. The compound of claim 1, wherein Ar is a phenyl ring.

3. The compound of claim 1, wherein $R^1$ is a hydroxyl group.

4. The compound of claim 3, wherein the $R^1$ hydroxyl group is acylated.

5. The compound of claim 4, wherein the acyl group is valerate.

6. The compound of claim 1, wherein X is a methyl group.

7. The compound of claim 1, wherein X is a methyl group and Ar is a phenyl group.

8. The compound of claim 7, wherein $R^1$ is a hydroxyl group.

9. The compound of claim 8, wherein $R^1$ is a hydroxyl group that is acylated with an acyl group.

10. The compound of claim 9, wherein the acyl group is valerate.

11. An anthracycline preparable by adding electrophilically, 3-O-benzyl-L-fucal in which a hydroxyl group at C-4 is blocked with a halosubstituted acyl group, to an anthracyclinone.

12. A compound having a formula:

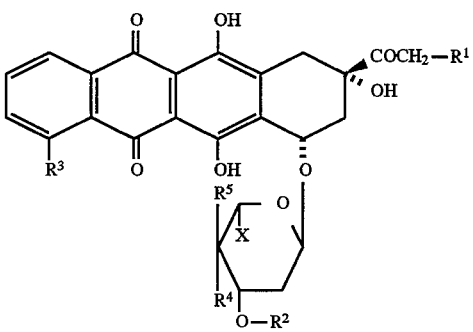

wherein $R^1$ is a hydrogen or hydroxyl group;

$R^2$ is $CH_2$—Ar, where Ar is an aryl group;

$R^3$ is a hydrogen or $OCH_3$ group;

$R^4$ is either a hydrogen or hydroxyl group;

$R^5$ is either a hydrogen or hydroxyl group; and

X is either a methyl group or a fluoro-methyl group.

13. The compound of claim 12, further defined as being 7-O-(3-O-benzyl-2, 6-dideoxy-α-L-lyxo-hexopyranosyl) adriamycinone.

14. The compound of claim 12, further defined as being 7-O-(3-O-benzyl-2,6-dideoxy-α-L-lyxo-hexopyranosyl)-14-O-valeroyl-adriamycinone.

15. The compound of claim 12, wherein $R^1$ is a hydroxyl group.

16. The compound of claim 15, wherein the $R^1$ hydroxyl group is an acylated hydroxyl group and the acyl group is valerate.

17. A compound further defined as 7-O-(3-O-benzyl-2, 6-dideoxy-α-L-lyxo-hexopyranosyl) adriamycinone (WP 546) or 7-O-(3-O-benzyl-2,6-dideoxy-α-L-lyxo-hexopyranosyl)-14-O-valeroyl-adriamycinone (WP 549).

18. The compound of claim 17, further defined as 7-O-(3-O-benzyl-2, 6-dideoxy-α-L-lyxo-hexopyranosyl) adriamycinone (WP 546).

19. The compound of claim 17, further defined as 7-O-(3-O-benzyl-2,6-dideoxy-α-L-lyxo-hexopyranosyl)-14-O-valeroyl-adriamycinone (WP 549).

* * * * *